United States Patent [19]

Thompson et al.

[11] Patent Number: 4,594,322

[45] Date of Patent: * Jun. 10, 1986

[54] GLUCOSE OR MALTOSE FROM STARCH

[75] Inventors: Gregory J. Thompson, Waukegan; Kaung-Far Lin, Arlington Heights; David W. Penner, Hoffman Estates, all of Ill.

[73] Assignee: UOP Inc., Des Plaines, Ill.

[ * ] Notice: The portion of the term of this patent subsequent to Apr. 16, 2002 has been disclaimed.

[21] Appl. No.: 608,837

[22] Filed: May 10, 1984

Related U.S. Application Data

[63] Continuation-in-part of Ser. No. 486,479, Apr. 19, 1983, abandoned.

[51] Int. Cl.$^4$ .................... C12P 19/22; C12P 19/24; C12P 19/20; C12P 7/14
[52] U.S. Cl. ........................ 435/95; 435/94; 435/96; 435/162; 435/813

[58] Field of Search .................. 435/95, 96, 94, 162, 435/813

[56] References Cited

U.S. PATENT DOCUMENTS

| 4,243,750 | 1/1981 | Muller et al. | 435/162 |
| 4,306,023 | 12/1981 | Crombie | 435/161 |
| 4,511,654 | 4/1985 | Rohrbach et al. | 435/95 |

*Primary Examiner*—Lionel M. Shapiro
*Attorney, Agent, or Firm*—Thomas K. McBride; John F. Spears, Jr.; Eugene I. Snyder

[57] ABSTRACT

A process for obtaining glucose from thinned starch by partially hydrolyzing the latter to give from 50% to 92% glucose followed by separation of the hydrolysis product to afford a glucose-enriched product with recycling of the glucose-depleted stream affords benefits unattainable by conventional commercial processes. Substantial reductions in process time and reversion products and a substantial increase in productivity are among some of the benefits.

11 Claims, 2 Drawing Figures

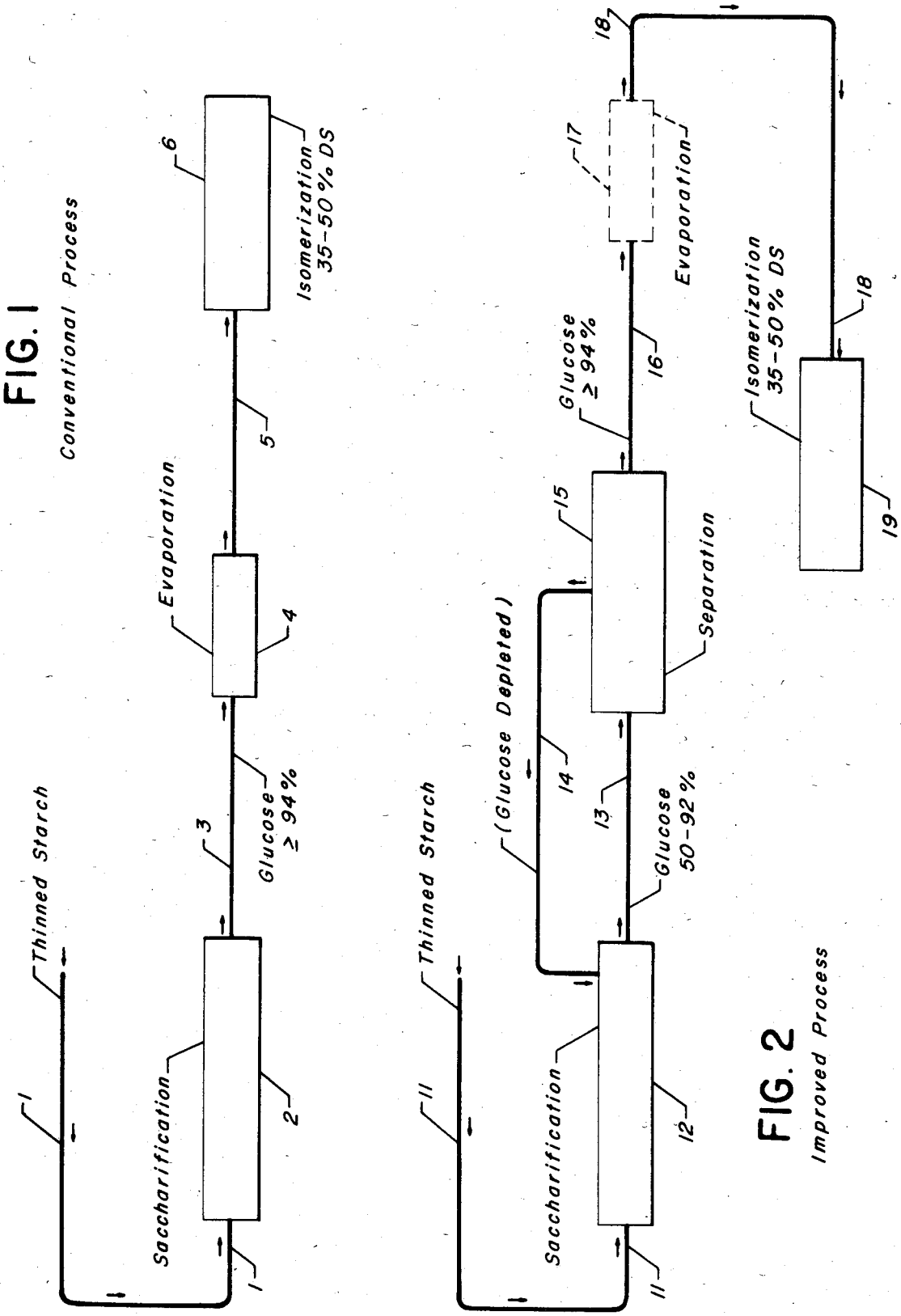

GLUCOSE OR MALTOSE FROM STARCH

CROSS-REFERENCE TO RELATED APPLICATION

This application is a continuation-in-part of our copending application Ser. No. 486,479, filed Apr. 19, 1983, abandoned which is incorporated herein by reference.

BACKGROUND OF THE INVENTION

The preparation of glucose from starch is a commercially important process, especially because of the subsequent use of glucose as a feedstock in its enzyme-catalyzed isomerization to fructose. The conventional scheme for glucose production is depicted in FIG. 1.

In FIG. 1 thinned starch, 1, which is a partially hydrolyzed starch more completely defined below, is the feedstock, at a dry solids (DS) level of about 30–40%, entering a saccharification or hydrolysis reactor zone, 2, where it undergoes enzyme-catalyzed hydrolysis using a glucose-forming enzyme, for example, amyloglucosidase (glucoamylase), hereafter referred to as AG. An essential feature of present processes is that hydrolysis is continued until maximum glucose formation is attained, which corresponds to about 94–96% glucose in the product stream, 3, when using a feedstock containing about 30% dry solids. Although only one reactor zone is depicted for saccharification, this is but one embodiment, and a plurality of reactor zones in series may be used in other embodiments.

Effluent, 3, from 2 containing more than about 94% glucose (on a dry solids basis) is then concentrated, where necessary, in an evaporation zone, 4, to afford a product stream, 5, containing from about 35% to about 50% dry solids. This product stream, 5, is typically the feedstock entering an isomerization reactor zone, 6, in which glucose is enzymatically converted to fructose by glucose isomerase.

The preparation of maltose from starch is also a commercially important process with a scheme analogous to that depicted in FIG. 1, the major difference being that the thinned starch is hydrolyzed with a maltose-producing enzyme. Beta-amylase is presently largely, if not exclusively, the maltose-producing enzyme used. Additionally, somewhat different alpha-amylases may be used to produce thinned starch with differing, but analogous properties depending upon whether maltose or glucose is desired.

The invention herein is directed toward both glucose and maltose production. However, solely for the sake of brevity the description herein will be directed toward glucose production, with it being clearly understood that a similar description directed toward maltose production is subsumed therein.

Several disadvantages attach to the aforedescribed process. One disadvantage, generic to any run to maximum conversion, is the increased cost consequent to the process time requirements for attaining maximum conversion; the longer the time for such conversion to be established, the more costly, hence more disadvantageous, is the process. Because glucose represses enzyme activity by complexing with AG, this leads to a decrease in hydrolysis rate as glucose accumulates and further increases process time. Another disadvantage, characteristic of the AG-catalyzed hydrolysis of thinned starch, is that the formed glucose, a monosaccharide, reverts to disaccharides, among which is isomaltose. Because isomaltose is a refractory disaccharide, that is, it is not readily hydrolyzed, and because it is bitter, it is a highly undesirable component of a glucose feedstock used for fructose production. Yet the longer the reaction time, the higher the glucose level, the higher is the isomaltose concentration in the product.

Because present commercial processes for production of high fructose corn syrup by isomerization of glucose utilize a glucose feedstock containing at least 94% glucose, a constraint of any new or modified process for production of glucose is that it afford comparable glucose levels. The process of this invention achieves such results by a method where hydrolysis proceeds to an extent short of maximum glucose formation to afford a product from which at least 94% glucose can be obtained by separation, with recycling of the stream from the separation stage depleted in glucose to the enzyme-catalyzed hydrolytic stage. By carrying out hydrolysis to a state substantially short of maximum glucose formation, the invention herein achieves a considerable saving in time and affords glucose with substantially lower levels of reversion products.

Therefore, an advantage of our invention is that it affords a substantial reduction in process time. Another advantage accompanying a reduction in time is that the process which is our invention affords glucose with less reversion products than the prior art processes.

Still other advantages accrue from characteristics of enzyme-catalyzed hydrolysis of thinned starch which the presently used commercial processes cannot take advantage of. When a feedstock for AG-catalyzed hydrolysis is increased in dry solids it is found that enzyme stability, as measured by its half-life, also increases. It is also found that the rate of glucose formation increases with increasing dry solids. Both of these characteristics are quite favorable, yet cannot be used in present commercial processes because increasing dry solids also leads to a lower maximum glucose level accompanied by increased reversion products.

In contrast to the prior art methods, the process of the instant invention is able to advantageously utilize the favorable characteristics of increased enzyme stability and increased glucose formation rate without any accompanying disadvantage of increased reversion products. Thus, in this sense our invention is truly synergistic; it incorporates the beneficial effects without incorporating the detrimental one.

The characteristic of using immobilized AG in hydrolyzing thinned starch is that it typically affords less than 94% glucose at equilibrium. Thus, immobilized AG can be used only with difficulty in present commercial processes. Therefore, yet another advantage of the instant invention is that it readily permits the use of an immobilized AG.

Still another advantage of the process described herein is that it affords a substantial increase in productivity, defined as the amount of glucose formed per unit of enzyme. This productivity increase results, in part, from recycling the enzyme incidental to the recycle stage of the process (where soluble AG is used), as well as a longer half-life (where either a soluble or immobilized AG is used).

The glucose level in our process as described is at least 94%. However, glucose levels of greater than 99% may be readily achieved by suitably varying process variables. Thus, still another advantage of our process is that it may be tailored to continually produce high-purity glucose, with a glucose purity greater than 99% being attainable.

Yet another advantage of the process which is our invention is that it can afford virtually complete conversion of starch to glucose.

It should be readily apparent from the multitude of the aforementioned advantages that our invention represents a substantial advance in the art of producing glucose at levels of about 94% and greater by AG-catalyzed hydrolysis of thinned starch.

SUMMARY OF THE INVENTION

The purpose of this invention is to obtain glucose (maltose) from the enzyme catalyzed hydrolysis of thinned starch by a more efficient process. An embodiment is a process whereby a feedstock of thinned starch is hydrolyzed to afford glucose (maltose) below maximum formation levels, separating the products into a glucose (maltose)-enriched stream and a glucose (maltose)-depleted stream, recovering the glucose (maltose)-enriched stream, and recycling the glucose (maltose)-depleted stream to a hydrolysis zone. In a more specific embodiment the thinned starch is hydrolyzed until the products contains from about 70% to about 80% glucose (maltose). In a still more specific embodiment, the glucose (maltose)-enriched stream contains at least about 94% glucose (maltose).

DESCRIPTION OF THE INVENTION

This invention is a process for obtaining glucose or maltose from thinned starch which represents a radical departure from prior art methods. One point of departure is the partial hydrolysis of thinned starch. That is to say, whereas the prior art methods hydrolyzed thinned starch for a time sufficient to attain maximum formation of glucose, the process herein continues hydrolysis for a substantially lesser period of time, thereby affording a product which contains less than maximum levels of glucose. Yet another point of departure is the separation of the hydrolysis product into a glucose-enriched stream and a glucose-depleted stream with recycling of the latter to the hydrolysis zone. The process herein is conveniently summarized by the flow diagram depicted in FIG. 2.

In FIG. 2, a thinned starch, 11, as defined within, usually containing from about 30% to about 45% dry solids, is the feedstock for a saccharification reactor zone, 12. Although only one reactor zone is depicted, this is but one embodiment. Embodiments where a plurality of reactor zones are used in the saccharification stage are contemplated and are to be considered within the scope of the claimed invention. Effluent, or product stream 13, from the saccharification zone contains glucose at levels, based on total solids, from about 50% to about 92%, and this is used as the feedstock for the separation zone, 15. Separation is here depicted as a single stage, but embodiments employing multistage separation are variants within the scope of this invention.

The effluent from the separation zone is in two product streams, one being enriched in glucose, 16, to contain at least 94% glucose (on a total solids basis), the other being a glucose-depleted stream, 14. This latter is then recycled to the saccharification reactor zone, 12.

Where the glucose-enriched stream 16 is ultimately to be used as the feedstock for a glucose isomerase reactor, it is then sent to an evaporation zone, 17, where necessary, to afford stream 18 containing from about 35% to about 50% dry solids. Said stream 18 then is utilized as the feedstock for an isomerization reactor zone 19 converting glucose to fructose. However, it is to be clearly understood that the glucose-enriched stream may serve as the glucose source for purposes other than use as a feedstock for isomerization to fructose. Other purposes to which the glucose may be put include hydrogenation to sorbitol, fermentation to ethanol, and a sweetener in food.

Where the product is maltose there is no isomerization reactor zone 19 as depicted in FIG. 2. The maltose-enriched stream corresponding to 16 is either used as is or sent to an evaporation zone 17 to afford more concentrated solutions of maltose, or even dry maltose.

In the initial part of our process a feedstock of thinned starch is enzymatically hydrolyzed by a glucose-producing enzyme, chiefly AG, to a product containing from about 50% to about 92% glucose. For the purpose of this application, thinned starch is a partially degraded starch containing a minor proportion of monosaccharides, up to about 10% but generally less than about 4%, and a distribution of polysaccharides, where from about 20% to about 70% are present as disaccharides ($DP_2$) through heptasaccharides ($DP_7$), with from about 30% to about 80% present as $DP_8$ and higher molecular weight polysaccharides. This hydrolysis step often is referred to as saccharification. The AG used may be soluble, in which case it is recycled with the glucose-depleted stream, or it may be an immobilized AG. In either case pullulanase or alpha-amylase, or both, may be present in the thinned starch feedstock to aid hydrolysis. The temperature at which the enzymatic hydrolysis is conducted depends upon the thermal stability of the enzyme used, but generally the temperature is between about 40° and about 80° C., with the temperature of about 60° C. being the most usual one. However, the AG from at least one microorganism is known to be sufficiently thermostable to allow the process to be run at temperatures even up to about 100° C.

A desirable consequence of hydrolyzing thinned starch to a product containing from about 50% to about 92% glucose is a substantial reduction in reaction time. Thus, hydrolysis to a product containing 50% glucose may take less than one-fourth of the time needed to attain 94% glucose, hydrolysis to 90% glucose may take only one-half the time, and even hydrolysis to 92% glucose may take only three-fifths the time. Another desirable consequence is a decided improvement in organoleptic characteristics through substantial reduction of the bitter principal, isomaltose; hydrolysis to 50% glucose may be accompanied by only about one-fourth as much isomaltose as accompanies the 94% glucose product.

A feedstock of thinned starch containing from about 30% to about 45% dry solids is conventional in the industry, although our process is not limited thereto. However, a dry solids level from about 35% to about 45% is preferred in the practice of this invention to obtain the full advantage of the salutary effect of higher dry solids on enzyme stability and the rate of glucose formation.

Prior art methods continue the hydrolysis to maximum glucose formation, which corresponds to glucose levels of about 94%. However, an essential feature of our process is continuation of hydrolysis to a product containing from about 50% to about 92%, but more usually not more than about 90% glucose. A product containing from about 60% to about 85% glucose is desirable, and one containing from about 70% to about 80% glucose is particularly preferred.

The hydrolysis product is then separated into a glucose-enriched stream and a glucose-depleted stream. Where the glucose-enriched stream is used as the feedstock for isomerization to fructose and stream will contain at least about 94% glucose, since present processes for forming fructose from glucose require a feedstock containing at least about that level of glucose purity.

Where a feedstock of less than 94% glucose is acceptable, a less stringent separation to afford lower purity glucose may be effected. As a practical matter, the glucose-enriched stream generally will contain at least about 90% glucose. It also must be understood that separation may be performed to obtain higher purity glucose, i.e., 94+% glucose. In fact, our invention may be used to continually produce glucose of greater than 99% purity where such high purity material is desired.

Generally, separation will occur in a single stage. However, multi-stage separation may be advantageous in some circumstances, and these are considered to be within the scope of our invention. In any event, the glucose-enriched stream from the separation zone stage is recovered for subsequent use or processing.

Any method of separation which is selective for glucose relative to disaccharides and higher polysaccharides is suitable. Where maltose, a disaccharide, is formed the separation needs to be selective relative only to higher polysaccharides. For example, a membrane-based separation may be effectively utilized. As another example, a separation based on solid adsorbents may be utilized. Examples of the latter include aluminas, silicas, various clays, zeolites, and so forth. Still another method of separation is selective crystallization of glucose from the saccharide mixture. Glucose also may be separated by dialysis of the product stream. Still other methods of separation which may be used in the process herein include solvent extraction and supercritical extraction, to cite but two further exemplary methods.

An integral part of this invention is the recycling of the glucose-depleted stream to a hydrolysis zone. The particular hydrolysis zone which is the entry point for the recycled stream will depend on process parameters such as reactor configuration, the activity of the particular enzyme, whether the enzyme is soluble or immobilized, the enzyme concentration if soluble, desired purity of the product, the particular means of separation, and so forth. Under many process conditions the location of the recycle point may be varied broadly without substantial impact. But in any event it should be clear that the determination of a suitable hydrolysis zone will depend upon the parameters of any particular process with its determination well within the capability of the skilled worker.

The examples which follow are merely illustrative of this invention and are not intended to limit or restrict it in any way.

Thinned starch used as the feedstock was Maltrin-150, a typical analysis for which showed about 1% glucose, 3% $DP_2$, 6% $DP_3$, 4% $DP_4$, 4% $DP_5$, 9% $DP_6$, 16% $DP_7$, and 58% $DP_8$ and higher.

Glucoamylase was assayed as follows. To 4 ml of a starch solution, 30% dry solids, was added 25 microliters of the enzyme solution, and the mixture was incubated 30 minutes at 60° C. Hydrolysis was quenched by the addition of 1 ml 0.2 N NaOH, and the mixture was cooled. The amount of glucose formed was determined using a glucose analyzer. The number of grams of glucose produced per hour is the AG activity expressed in Miles units.

EXAMPLE 1

A solution of AG (77 units/liter) at pH 4.2 in glucose solutions containing varying levels of dry solids was maintained at 60° C. Aliquots were withdrawn periodically and assayed for AG activity. The enzyme half-life was found to be 4.8, 12.3, and 21.9 days at dry solids levels of 30%, 44% and 55%, respectively. Thus, enzyme stability as measured by half-life at 60° C. is increased over 4.5-fold in going from 30% to 55% dry solids.

EXAMPLE 2

Feedstocks of Maltrin-150 of different dry solids (DS) level at pH 4.2 containing AG at 77 units per liter were hydrolyzed at 60° C. Glucose concentration as determined by high pressure liquid chromatography was monitored with time, the results being summarized in the accompanying table.

TABLE 1

| Time | Glucose Concentration With Hydrolysis Time | | |
|---|---|---|---|
| | Glucose conc., grams/liter | | |
| (hours) | 30% DS | 44% DS | 55% DS |
| 5 | 260 | 290 | 305 |
| 10 | 320 | 405 | 425 |
| 20 | 330 | 500 | 540 |
| 40 | 340 | 525 | 600 |
| 80 | 340 | 525 | 600 |

The results clearly show that glucose production rates increases with increasing dry solids level of feedstock.

EXAMPLE 3

A feedstock of Maltrin-150, 30% dry solids, at pH 4.2 and containing AG at 77 units per liter was hydrolyzed at 60° C. Product was analyzed for glucose, total disaccharides ($DP_2$), and isomaltose. Results using two different lots of AG are summarized in the table below.

TABLE 2

| Glucose, Disaccharide, and Isomaltose Production | | | |
|---|---|---|---|
| Time | Weight % | | |
| (hours) | glucose | disaccharides | isomaltose |
| | Run 1 | | |
| 2 | 28 | 8.5 | 0 |
| 4 | 58 | 9.0 | 0.6 |
| 6 | 72 | 4.5 | 0.9 |
| 8 | 88 | 4.0 | 0.9 |
| 10 | 90 | 4.5 | 1.3 |
| 12 | 92 | 4.8 | 1.3 |
| 20 | 94 | 5.8 | 2.2 |
| 30 | 94 | 7.0 | 3.4 |
| | Run 2 | | |
| 1.8 | 45.1 | 17.3 | 0 |
| 4.7 | 69.0 | 10.8 | 0 |
| 5.6 | 74.4 | 7.5 | 0 |
| 7.5 | 80.9 | 4.5 | 0 |
| 13.0 | 91.1 | 3.2 | 0.0 |
| 20.0 | 93.5 | 3.4 | 0.8 |
| 48.0 | 94.8 | 4.1 | 1.6 |

Thus, relative to the time needed to attain a 94% glucose product attainment of a 90% glucose product takes about half the time, and attainment of a 92% glucose product takes about 60% of the time.

These results also clearly show the accumulation of isomaltose during the latter stages of conversion.

EXAMPLE 4

This example compares results from a once-through reactor, i.e., a conventional operation in which thinned starch is hydrolyzed to about 94% or greater glucose, with a closed-loop system where reactor effluent is sent to a membrane, a glucose-enriched product stream is drawn off, and the glucose-depleted stream is recycled to the beginning of the reactor. All hydrolyses were performed at 60° C., pH 4.5–5.5. Run A is the conventional, once-through reactor; both Runs B and C are closed-loop systems, with B using a cellulose acetate membrane having a 10,000 molecular weight cutoff operating at 60° C., 150 psig, and C using a polyelectrolyte membrane with a 500 molecular weight cutoff operating at 60° C., 300 psig, both supplied by Amicon Co. under their designations YM10 and UM05, respectively. Results are listed in Table 3, where $DP_1$ represents total monosaccharides, nearly all of which is glucose, $DP_2$ represents disaccharides, $DP_{4+}$ are polysaccharides of four or more units, and DS is dry solids. For Runs B and C reactor effluent, product and recycle stream analyses are equilibrium values.

TABLE 3
Comparison of Once-Through (Single Pass) Reactor With Closed Loop, Recycle Reactor

|  | Run A | Run B | Run C |
|---|---|---|---|
| Enzyme (AG) dosage, units/liter | 77 | 34 | 58 |
| Residence time, hours | 48 | 14 | 20 |
| Feedstock Composition (%) | | | |
| DS | 30.0 | 26.1 | 24.7 |
| $DP_1$ | 1.0 | 1.2 | 1.6 |
| $DP_2$ | 4.5 | 4.3 | 3.9 |
| $DP_{4+}$ | 87.5 | 87.8 | 88.3 |
| Reactor Effluent | | | |
| DS | 33.0 | 27.0 | 30.4 |
| $DP_1$ | 95.7 | 90.5 | 83.4 |
| $DP_2$ | 4.1 | 2.9 | 4.4 |
| $DP_{4+}$ | 0.2 | 6.3 | 11.6 |
| Product Stream | | | |
| DS |  | 26.1 | 24.7 |
| $DP_1$ |  | 93.6 | 98.0 |
| $DP_2$ |  | 3.1 | 2.0 |
| $DP_{4+}$ |  | 2.9 | 0.0 |
| Recycle Stream | | | |
| DS |  | 27.4 | 34.2 |
| $DP_1$ |  | 89.9 | 82.5 |
| $DP_2$ |  | 3.5 | 3.8 |
| $DP_{4+}$ |  | 6.3 | 13.1 |

EXAMPLE 5

A kinetic model was developed from experimental data which not only closely reproduced existing experimental data but also had reliably high predictive ability. Among the variables (experimental parameters) accommodated by the model were feedstock (thinned starch) composition, enzyme dosage, reactor residence time, membrane type and operating conditions. Output included glucose and isomaltose concentration in the product stream. The feedstock of thinned starch had 30.6 weight percent dry solids with 1.2% $DP_1$, 4.8% $DP_2$, and 87% $DP_{4+}$. Run A represents a once-through reactor, and Runs B and C represent a closed-loop recycle reactor using the polyelectrolyte membrane described in the prior example with the glucose-depleted stream recycled to the top of the reactor. Reactor effluent and product compositions are equilibrium values.

TABLE 4
Isomaltose Accumulation

|  | Run A | Run B | Run C |
|---|---|---|---|
| AG concentration, units/liter | 77 | 9 | 18 |
| Residence time, hours | 48 | 10 | 10 |
| Reactor effluent: | | | |
| % glucose | 95.7 | 74 | 87.3 |
| % isomaltose | 1.66 | 0.7 | 1.85 |
| Product: | | | |
| % glucose |  | 95.5 | 97.2 |
| % isomaltose |  | 0.34 | 0.73 |

These data clearly show that the closed-loop, recycle process produces glucose at as high concentration as that from a conventional, once-through reactor at substantially lower enzyme dosage, with one-fourth the isomaltose content. In fact, Run C shows that one can increase glucose in the product to over 97% (using one-fourth the enzyme concentration) and still have less than half the isomaltose content as that from the conventional process.

EXAMPLE 6

In this example the aforementioned kinetic model was used to determine the effect of recycle location on glucose and isomaltose concentration in the steady state product and reactor effluent streams. Data are summarized in Table 5, where "reactor volume" refers to the percent reactor volume prior to the recycle location; 0 represents the top, 100 represents the bottom of the reactor. Thinned starch feedstock had the composition of that in the foregoing example; reactor time was 10 hours and the polyelectrolyte membrane of Example 4 was used under the stated conditions.

TABLE 5
Effect of Recycle Point on Product Composition

|  | Reactor Volume | | | | | |
|---|---|---|---|---|---|---|
|  | 0 | 30 | 50 | 70 | 90 | 95 |
| AG concentration: 18 u/l | | | | | | |
| Reactor effluent | | | | | | |
| glucose | 87.4 | 88.0 | 87.0 | 85.0 | 73.0 | 57.0 |
| isomaltose | 1.85 | 1.8 | 1.7 | 1.3 | 0.6 | .25 |
| Product | | | | | | |
| glucose | 97.2 | 97.2 | 97.2 | 96.9 | 96.9 | 90.7 |
| isomaltose | 0.73 | 0.71 | 0.66 | 0.55 | 0.27 | 0.13 |
| AG concentration: 77 u/l | | | | | | |
| Reactor effluent | | | | | | |
| glucose | 91.5 | 91.5 | 91.5 | 91.5 | 92.3 | 91.0 |
| isomaltose | 4.75 | 4.8 | 4.7 | 4.4 | 3.35 | 2.5 |
| Product | | | | | | |
| glucose | 96.9 | 96.9 | 96.9 | 97.0 | 97.3 | 97.4 |
| isomaltose | 1.73 | 1.74 | 1.70 | 1.59 | 1.22 | 0.93 |

The results in the table reflect the fact that at high AG concentration the product composition is rather insensitive to recycle point throughout, and at lower enzyme concentration no substantial change in product composition is seen when the recycle point is between 0–90% of reactor volume. The overall conclusion is that recycle location will be a process choice depending upon other process parameters such as enzyme concentration, residence time, separation means used, product composition desired, etc.

EXAMPLE 7

These data generated by the kinetic model show the advantages, absent in a once-through reactor, accruing from a feedstock with high dry solids used in a closed loop, recycle process. Feedstock had the composition of Example 5 with only the dry solids (weight percent) varying. The recycle reactor utilized the polyelectrolyte membrane of Example 4 under the conditions stated therein.

TABLE 6
Effect of Dry Solids Variation

|  | Once-through reactor | | Closed loop recycle reactor |
| --- | --- | --- | --- |
| % Dry solids | 30 | 40 | 40 |
| Residence time, hours | 48 | 71 | 10 |
| AG concentration, units/liter | 77 | 77 | 18 |
| Product, wt. %: | | | |
| glucose | 95.7 | 93.6 | 95.6 |
| isomaltose | 1.7 | 2.2 | 0.7 |

In a once-through reactor residence time is unacceptably long and isomaltose concentration is unacceptably high using 40% dry solids feedstock, whereas in the closed loop recycle reactor configuration residence time is reduced 7-fold, isomaltose concentration 3-fold, and enzyme concentration 4-fold.

What is claimed is:

1. A process for obtaining a sugar which is either glucose or maltose from thinned starch comprising hydrolyzing a feedstock of thinned starch under the action of a glucose- or maltose-producing enzyme to a product containing from about 50% to 92% of said sugar, separating the product into a sugar-enriched stream, containing at least 90% sugar, and a sugar-depleted stream, recovering the sugar-enriched stream, and recycling the sugar-depleted stream to a hydrolysis zone.

2. The process of claim 1 where the feedstock contains from about 30% to about 45% dry solids.

3. The process of claim 1 where the product of hydrolysis contains from about 60% to about 85% sugar.

4. The process of claim 3 where the product of hydrolysis contains from about 70% to about 80% sugar.

5. The process of claim 1 where the hydrolysis is catalyzed by a soluble enzyme.

6. The process of claim 1 where the hydrolysis is catalyzed by an immobilized enzyme.

7. The process of claim 1 where the enzyme is amyloglucosidase and the sugar is glucose.

8. The process of claim 1 where the enzyme is beta-amylase and the sugar is maltose.

9. The process of claim 1 where the sugar-enriched stream contains at least about 94% sugar.

10. The process of claim 1 where a membrane-based separation is utilized.

11. The process of claim 1 where a solid adsorbent-based separation is utilized.

* * * * *